United States Patent [19]

Doll

[11] 4,134,396

[45] Jan. 16, 1979

[54] METHOD AND APPARATUS FOR DEVELOPING INTERMITTENT VENOUS BLOOD FLOW AND MEASURING TOTAL BLOOD FLOW

[75] Inventor: Henri G. Doll, New York, N.Y.

[73] Assignee: Doll Research, Inc., New York, N.Y.

[21] Appl. No.: 799,219

[22] Filed: May 23, 1977

[51] Int. Cl.$^2$ ............................................. A61B 5/02
[52] U.S. Cl. ............................................. 128/2.05 F
[58] Field of Search ................................. 128/2.05 F

[56] References Cited

U.S. PATENT DOCUMENTS

| | | | |
|---|---|---|---|
| 3,507,270 | 4/1970 | Ferrier | 128/2.05 F |
| 3,659,591 | 5/1972 | Doll | 128/2.05 F |
| 3,751,980 | 8/1973 | Fryer | 128/2.05 F |
| 3,920,004 | 11/1975 | Nakayama | 128/2.05 V |

Primary Examiner—William E. Kamm

Attorney, Agent, or Firm—Kenyon & Kenyon, Reilly, Carr & Chapin

[57] ABSTRACT

Normal steady venous return flow in a limb is rendered intermittent by means to occlude the venous system in the limb for a first period of time while permitting pulsatile arterial inflow to the limb. Means to release the venous system for a second period of time allows a rapid exponentially decreasing outflow of the blood that was pooled in the venous system during the first period. The exponentially decreasing outflow may be detected by a flowmeter responsive only to pulsatile flow. The flowmeter may also detect unwanted heart-synchronized signals. The latter may be cancelled from the venous blood flow signal by detecting and storing heart-synchronized signals during at least a part of the first period (of zero venous flow) and subtracting the stored signals from signals detected during the second period.

13 Claims, 3 Drawing Figures

METHOD AND APPARATUS FOR DEVELOPING INTERMITTENT VENOUS BLOOD FLOW AND MEASURING TOTAL BLOOD FLOW

BACKGROUND OF THE INVENTION

1. Field of the Invention

The present invention relates to measurement of blood flow in a limb of a living being, and particularly to an improved apparatus and method adapted to measure total venous blood flow in a limb with a flowmeter responsive only to pulsatile flow.

2. Description of the Prior Art

The circulatory system in humans and other vertebrates includes an arterial network which distributes blood from the heart to the extremities and a venous network which conveys the blood back to the heart. The arterial and venous networks are connected through capillaries which distribute the blood to the tissues.

The normal flow of blood through the arteries can be divided into variable and steady components. The variable component usually is called pulsatile flow, modulated flow, or AC flow (by analogy to electric current). The steady component is called non-modulated, residual, or DC flow. The pulsatile arterial flow component can be further subdivided into forward flow (outward from the heart to the extremities) which occurs during the systolic period of the heart cycle, and reverse (retrograde) flow, which may occur during the diastolic period.

Due to the elasticity of the arterial blood vessels, there is typically a small, fairly steady residual forward flow during the post-diastolic period. This constant, or non-modulated, residual flow can comprise a significant percentage of the total net forward flow during each heart cycle. The total net forward arterial flow is the algebraic sum of the pulsatile systolic forward flow, the pulsatile diastolic flow, and the steady residual forward flow.

Since the capillaries provide a filtering barrier between the arteries and the veins, the venous return flow is essentially steady. Under equilibrium conditions, the venous outflow through a limb is equal to the arterial inflow.

Researchers and physicians investigating the condition of patients suffering from heart or circulatory impairment are often interested in determining the rate of blood flow perfusing a limb. Non-invasive blood flowmeters of the type described in U.S. Pat. No. 3,659,591; No. 3,759,247; and No. 3,809,070 (assigned to the assignee of this invention and incorporated herein by reference) have many advantages stemming from the use of sensing electrodes placed on the skin instead of subcutaneously. However, offset voltages are developed between the electrode surfaces and the skin layers. These offset voltages tend to drift with time and mask the signal contribution of steady flow components. Consequently, such instruments are designed to be not responsive to steady flow, only to variations in flow rate.

When such an instrument is used to measure normal blood flow in a limb, therefore, it will measure only the pulsatile components, both forward and retrograde, of the arterial flow. It will not respond either to the steady residual arterial flow or to the steady venous outflow.

SUMMARY OF THE INVENTION

It is the principal object of the present invention to provide a method and apparatus for modifying the venous blood flow in a limb of a living being to make is possible for a flowmeter to measure the totel venous outflow in the limb at a given location, said outflow being equal to the total arterial inflow.

A further object of the invention is to provide a method and apparatus for converting a total volume of steady venous flow in a limb for a preselected period of time into an equivalent volume for a shorter time of fully pulsatile flow which can be sensed, for example, by a non-invasive, constant-magnetic-field type of flowmeter.

Another object of the invention is to provide a method and apparatus for periodically occluding the venous network in a limb for first predetermined times, to permit blood flow through said venous network for second predetermined times between successive occlusion periods, and to measure the average venous blood flow and the rate of decay of the venous blood flow during the second periods of time.

These and other objects are achieved by a method for measuring blood flow through a limb of a living being which includes broadly the steps of:

(a) detecting blood flow signals at a preselected location along a limb of a living being;

(b) occluding the venous system of the limb at a position as close as possible to said detecting location, said occlusion being maintained for a first predetermined period of time while permitting at least systolic flow in the arterial system during said first period;

(c) unblocking the venous system at said position on said limb for a second predetermined period of time that is long enough to allow a release of at least part of the blood that was pooled in the venous system on the distal side of said position during said first period; and (d) processing the detected blood flow signals to provide a measure of the total blood flow during the total time of said first and second periods.

Preferably, the first and second time periods extend over pluralities of heart cycles, and the second time period is shorter than the first time period. In this way, only part of the blood pooled in the distal side of the limb during the first period will be released during the second period. This partial release is confined to the relatively steep initial part of the exponentially decreasing venous outflow, giving a stronger flow signal which is more accurately measurable than the relatively flat final part of the venous outflow.

The invention also includes apparatus for performing the above-described method. This apparatus includes means adapted to apply uniform predetermined pressure around the circumference of a limb of a living being for a plurality of heart cycles in combination with a conventional blood flow measuring system. The pressure applying means may include a pressure cuff of the type used in a conventional sphygmomanometer, a source of air under pressure, and air supply and exhaust lines equipped with valves for selectively inflating and deflating the pressure cuff. As mentioned earlier, the cuff should be positioned as close as possible to the flow detecting location.

A specific embodiment adapted to apply and release pressure around the limb automatically at timed intervals includes a trigger circuit actuated by the R-wave of an electrocardiac signal sensed at a suitable location on the skin of a living being. (The R-wave is the sharply-peaked portion of an electrocardiogram.) The trigger circuit delivers a sharp pulse, in synchronism with each R-wave, to a counter, and the counter delivers synchronizing signals in response to predetermined pluralities of pulses from the trigger circuit.

The apparatus further includes means for detecting the blood flow signals, a flowmeter for storing, averaging, and displaying the detected signals, and an inverter connected between the detecting means and the flowmeter to reverse selectively the incoming detected signals to the flowmeter. A first output from the counter is connected to the inverter. Pulses from this output cause successive equal groups of heart synchronized signals from the detecting means to be alternately reversed in polarity before cumulative storage in the flowmeter. Thus, each succeeding group cancels the preceding group.

Each synchronizing pulse from a second output of the counter actuates first an inlet valve that is connected between a pressure source and the cuff and then (after a delay) an exhaust valve that is connected between the cuff and either the atmosphere or a vacuum reservoir. A first duration generator maintains the inlet valve open for a first period at least long enough to inflate the cuff to a pressure below the local diastolic pressure at the cuff position. During this first period the exhaust valve remains shut.

After passing through a delay circuit, the same synchronizing pulse actuates a second duration generator which maintains the exhaust valve open for a second period long enough to release the pressure in the cuff.

The foregoing and other features of the present invention will be described in greater detail in connection with the preferred embodiment illustrated in the accompanying drawing.

DESCRIPTION OF THE PREFERRED EMBODIMENTS

Figure 1:
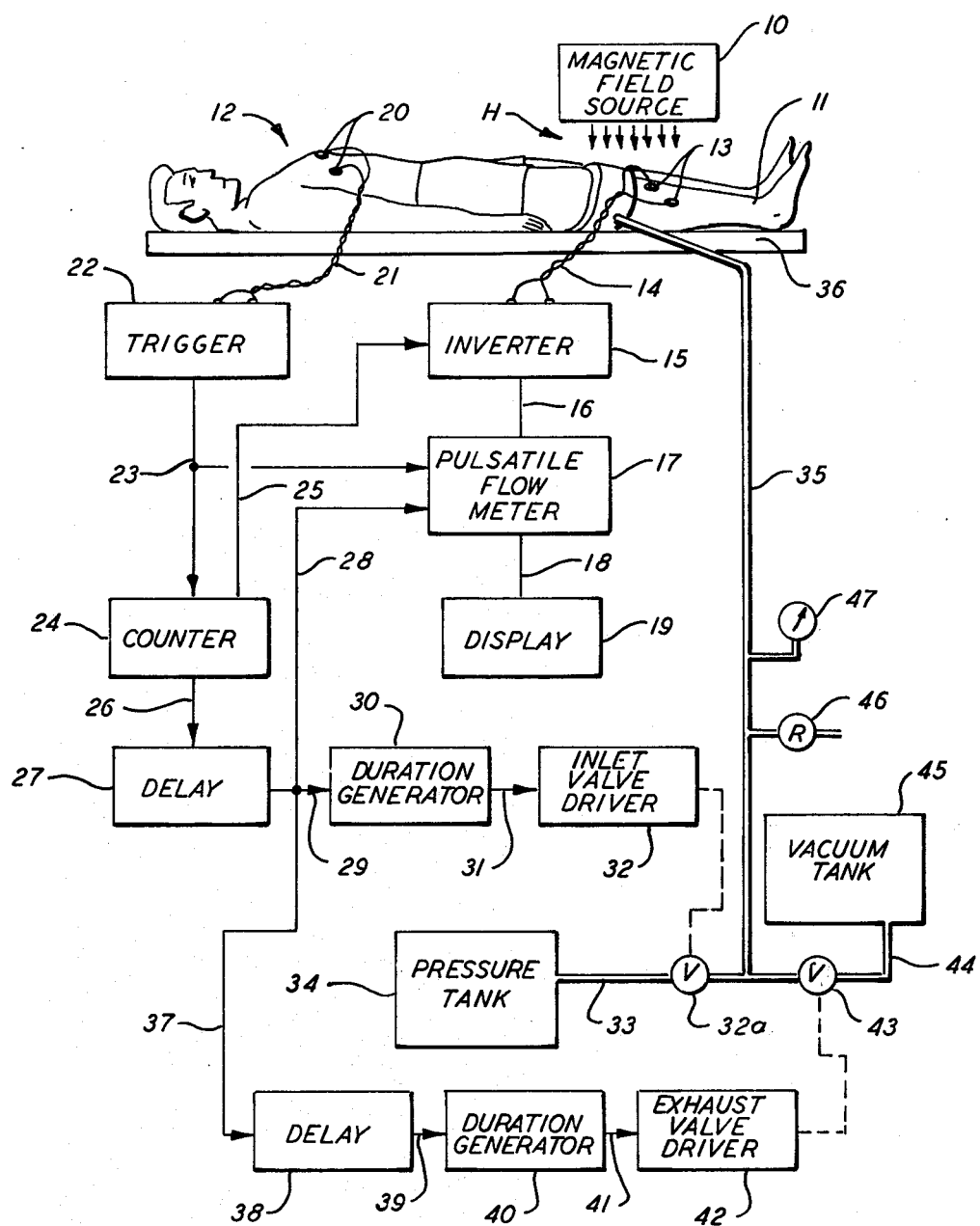
FIG. 1 illustrates in block diagram form a preferred embodiment of apparatus for measuring fully pulsatized venous blood flow in a limb of a living being.

Referring to FIG. 1, apparatus for performing the method of the invention includes, for example, a non-invasive blood flowmeter having a source 10 of a steady homogeneous magnetic field having sufficient strength to produce detectable electric signals on the skin of a limb 11 of a living subject 12 in response to blood flow in the limb. The magnetic source may be a direct current electromagnet or a permanent magnet which can be positioned so that the magnetic field H is directed transversely to the limb.

At least two first sensing means, in the form of electrodes 13, are positioned in circumferentially spaced relation on the skin of the limb within the magnetic field for detecting the blood flow signals in selected blood vessels according to known techniques. The measuring electrodes are connected by twisted leads 14 through a controlled inverter 15 and line 16 to a conventional measurement and control system such as pulsatile flowmeter 17, which is connected through line 18 to display 19. This system may be of the type disclosed in the previously mentioned U.S. Pat. No. 3,659,591, No. 3,759,247, and No. 3,809,070. Such a system includes circuits for cumulatively storing successive blood flow waveforms over a number of pressurization cycles to provide an averaged blood flow signal having random and extraneous noise components reduced to insignificant levels.

In order to provide synchronizing and clocking signals to the pulsatile flowmeter, a pair of second sensing means (auxiliary electrodes 20) are connected by a pair of twisted leads 21 to a trigger circuit 22. The auxiliary electrodes are placed on the skin of the subject at a location where a strong electrocardiac signal can be obtained. The trigger circuit is a pulse shaper, such as a Schmitt trigger, that produces a sharp pulse once each heart cycle in response to the R-wave.

Timing pulses from the trigger circuit are directed via line 23 directly to the pulsatile flowmeter, where they synchronize storage of successive cyclical flow signals detected by sensing electrodes 13. In addition, the timing pulses are also led over line 23 to operate a counter 24. The counter produces two output signals; a first synchronizing pulse after a selected number of heart cycles and a second synchronizing pulse after double the selected number of heart cycles. The first triggering signal is connected to inverter 15 by line 25. After every successive selected number of heart cycles, a first synchronizing pulse actuates the inverter alternately first to pass through unchanged and then to reverse the signals from electrodes 13. Thus every train of the selected number of "positive" signals will be followed by a train of an equal number of "negative" signals. In this way, heart synchronized arterial flow and local electrocardiac signals will be cancelled after every other first synchronizing pulse. Each second synchronizing pulse from the counter, as mentioned above, occurs simultaneously with every other first synchronizing pulse. This second synchronizing pulse, after passing via line 26 through a preset delay circuit 27, is used to control the alternate damming up and release of a venous blood pool in the limb being measured.

The purpose of delay circuit 27 is to adjust the occlusion and release of the venous system to coincide with a selected event in the arterial flow cycle in the limb as desired. It is optional, however, and may be omitted without affecting the operability of the system.

Coming from the output of delay circuit 27, each second synchronizing pulse is delivered to the pulsatile flowmeter via line 28. By another branch line 29, the triggering signals pass to a duration generator 30, which may be a conventinal monostable multivibrator. The output of generator 30 is connected by line 31 to an inlet valve driver 32 which actuates a valve 32a in a supply pipe 33 leading from a pressure source 34 to supply air under pressure through a connecting tube 35 to a pressure cuff 36. The cuff surrounds limb 11 at or on the proximal side of the location of measuring electrodes 13.

Finally, each second synchronizing pulse also passes via line 37 to a second delay circuit 38. The output of delay circuit 38 is connected by line 39 to a second duration generator 40 and thence via line 41 to an exhaust valve driver 42, which actuates a valve 43 in an exhaust line 44 leading from connecting tube 35 to a vacuum reservoir 45 (or alternatively, to the atmosphere).

The operation of the system is as follows. Occurrence of a second synchronizing pulse from counter 24 (delayed as desired in delay circuit 27) actuates inlet valve 32a for a period determined by duration generator 30. This period is selected to be long enough to pressurize cuff 36 to a predetermined value below the local diastolic pressure, for example 50 mm of mercury. This pressure is obtained by adjusting a relief valve 46 by use of pressure gauge 47 in accordance with known techniques. The period of duration generator 30 needs to be only long enough to establish the desired pressure in the cuff. Then valve 32a can shut, and the pressure will hold until exhaust valve 43 opens.

Each second synchronizing pulse also actuates valve 43, but only after a delay produced in delay circuit 38. This delay is equal to the predetermined plurality of heart cycles that the cuff is to remain pressurized. Valve 43 is then opened for a period determined by duration generator 40 that is long enough to completely exhaust the air from cuff 36. It is preferred to exhaust the air as quickly as possible by connecting the exhaust valve to a vacuum reservoir. This is not essential, however, and valve 43 may simply exhaust to the atmosphere.

At the end of an unpressurized period equal to the time between successive second synchronizing pulses minus the delay of circuit 38, another synchronizing pulse from the output of delay circuit 27 repressurizes the cuff and starts the sequence all over again.

As previously mentioned, each first synchronizing pulse actuates the inverter 15, with one pulse serving to reverse the polarity of the incoming flow signal from measuring electrodes 13 and the next pulse serving to change the polarity back.

Figure 2:
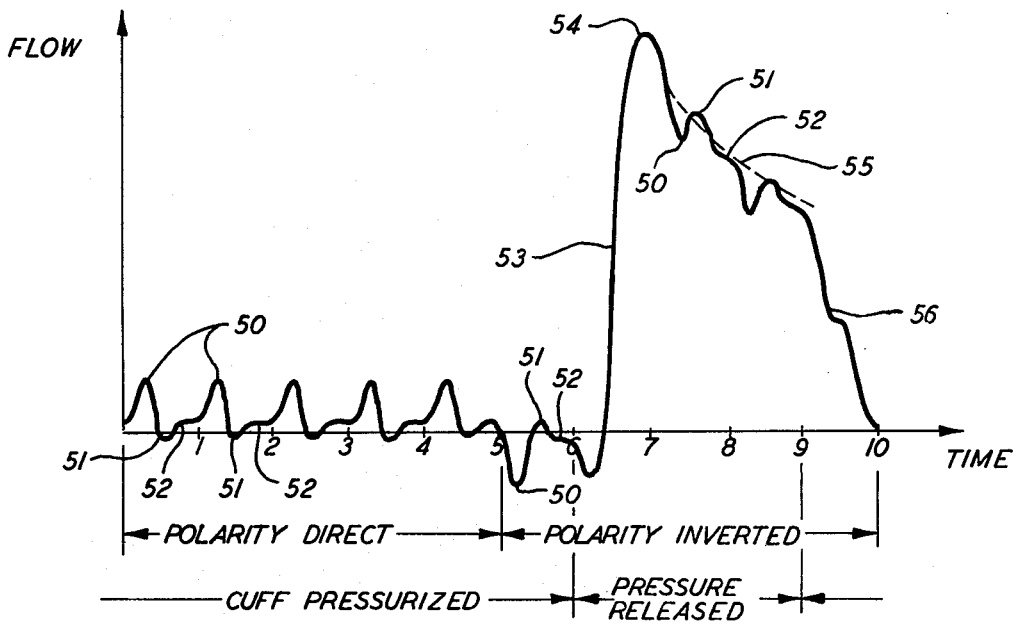
FIG. 2 represents a pulsatized blood flow pattern obtained by the method and apparatus of the invention and including both venous and arterial flow components.

The effect of the above-described operating cycle on the blood flow waveform entering the flowmeter from the inverter is illustrated in FIG. 2. In this diagram, time is plotted on the abscissa, and total aggregate blood flow rate at the sensing location is plotted on the ordinate. For illustration, the selected period between first synchronizing pulses is chosen, for instance, to be five heart cycles. For a reason that will be explained, the periods of cuff inflation and deflation are chosen to be approximately equal to seven and three heart cycles, respectively. In FIG. 2, cuff pressurization is initiated at heart cycle number 9 of each group of ten heart cycles, and pressure release occurs at cycle number 6 of the next group of ten heart cycles.

During the first period, when the cuff is inflated, there is no flow in the venous system (except for during the finite time, between cycles 9 and 10, required to shut off the flow). Since the cuff pressure is below diastolic, however, the arterial flow pattern is reduced only slightly. For each heart cycle, this pattern commences with a large inflow pulse 50, corresponding to the systolic pumping portion of the heart cycle. This pulse is followed by a small retrograde or reverse flow pulse 51, coincident with the diastolic portion of the heart cycle. Then during the post-diastolic or rest period of the heart cycle there is a small residual steady arterial distribution flow 52, lasting until the beginning of the next systolic pulse.

During the time that the cuff is inflated, the net arterial inflow of blood to the limb accumulates as a pool in the venous network, the various vessels expanding elastically to store this pool. When the cuff is rapidly deflated, this pooled blood is suddenly released, causing an initially large surge of venous outflow (rapidly rising line 53) which reaches a maximum valve 54 and then decreases exponentially along a curve corresponding to dashed line 55. In subjects where the venous system is weakened or relatively non-resilient, the venous outflow can be improved by the use of an elastic stocking on the limb.

The venous outflow would decrease exponentially to approach normal steady state venous flow if the venous pool were allowed to fully deplete. The outflow in the latter part of the exponential curve is difficult to detect, however, because it is small in amplitude and because it is almost constant. Therefore, it is desirable to make the outflow portion of each pressure and release cycle shorter than the venous storage portion; so that only partial depletion of the venous pool will occur. Thus, in the example of FIG. 2, the cuff is repressurized at cycle number 9, causing the exponentially decreasing venous outflow to be interrupted, as shown by sharply dropping line 56.

As a practical example, the delay time between pressurizing the cuff and exhausting the air may be from 5 to 25 seconds, while the period of pressure release, when venous outflow is permitted, may be from 3 to 5 seconds. These times are illustrative and are not meant to be limiting.

Within the conventional pulsatile flowmeter, the arterial flow signals during a first selected number of heart cycles (e.g., 5 in FIG. 2) are stored. These stored signals are then cancelled by the inverted arterial flow signals during the ensuing equal selected number of heart cycles. In a similar manner, local electrocardiac and other heart-synchronized signals (not shown) which are picked up by the measuring electrodes 13 are also stored, inverted, and cancelled. The remaining signal, representing the pulsatized venous flow waveform is illustrated in idealized form by curve 53, 54, 55, 56 in FIG. 3. This signal may be stored in a memory within the flowmeter and enhanced by repetitive cycles of cuff inflation and deflation. The flowmeter may also be augmented by a computer (not shown) programmed to apply the knowledge that the pulsatized venous outflow waveform is exponential in character to further enhance the signal over extraneous and non-cyclical noise components.

Figure 3:
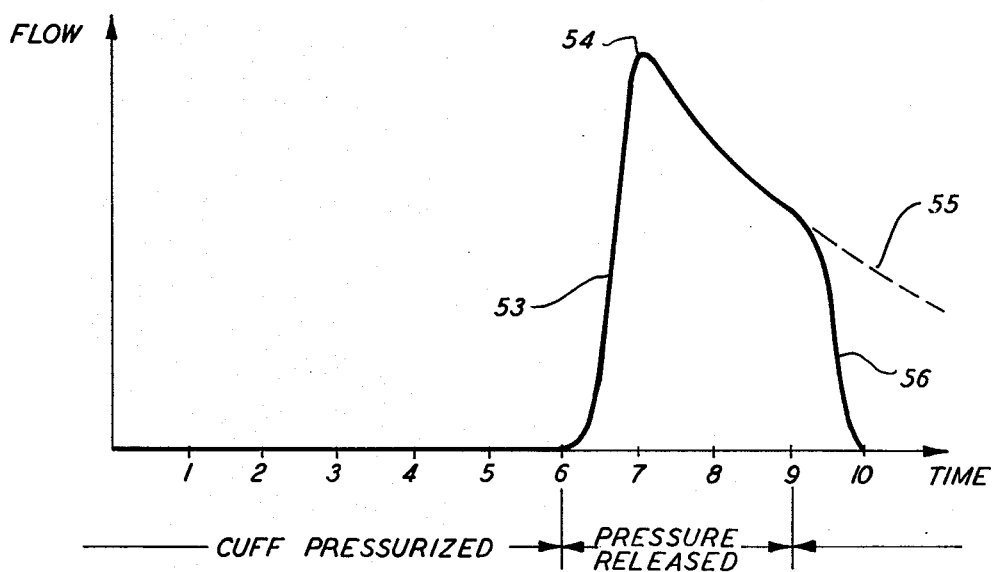
FIG. 3 illustrates the venous component of the blood flow pattern of FIG. 2.

The waveform of FIG. 3 is useful for medical analysis because the time constant of the exponential venous outflow curve gives an indication of the patency (defined as the ability to carry flow) of the veins in the limb near the cuff.

In addition, the integral of the venous outflow over one total cycle of cuff inflation and deflation, when divided by the time of such cycle, will yield the average blood flow rate perfusing the limb at the measurement location.

It will be appreciated that although cuff inflation and deflation periods of seven and three heart cycles, respectively, have been illustrated, the method of the invention can be practiced with longer periods and different time ratios, if desired. In fact, the preferred time between successive first triggering signals is about 10 heart cycles, rather than the 5 cycles used for simplicity in FIG. 2. With a larger number of heart cycles (up to the practical limits of venous bed elasticity) the relative amplitude of the arterial waveform compared with the venous waveform is reduced, and the times required to fully inflate and fully deflate the cuff become a smaller part of the total time of one measurement cycle. These factors both tend to increase the accuracy of measuring the venous flow.

It will be appreciated that other equivalent apparatus can be used to perform the method disclosed in this application without departing from the scope of the present invention.

What is claimed is:

1. A method for measuring blood flow in a limb of a living being comprising:
    (a) detecting blood flow signals at a first location along a limb of a living being;
    (b) occluding the venous system of the limb at a position as close as possible to the first location, said occlusion being maintained for a first predetermined period of time while permitting systolic flow in the arterial system during said first period;
    (c) unblocking the venous system at said position for a second predetermined period of time that is long enough to allow a release of part of the blood that was pooled in the venous system on the distal side of said position during said first period; and
    (d) cumulatively storing the detected blood flow signals for at least said second period to obtain a total blood flow value.

2. A method for measuring blood flow in a limb of a living being comprising:
    (a) detecting blood flow signals at a first location along a limb of a living being;
    (b) occluding the venous system of the limb at a position as close as possible to the first location, said occlusion being maintained for a first predetermined period of time while permitting systolic flow in the arterial system during said first period;
    (c) storing the detected blood flow signals for said first period;
    (d) unblocking the venous system at said position for a second predetermined period of time that is long enough to allow a release of part of the blood that was pooled in the venous system on the distal side of said position during said first period; and
    (e) subtracting the blood flow signals stored during at least a part of the first period from the blood flow signals detected in the second period; so that the arterial flow and local electrocardiac components of the decreasing blood flow signal during the second period are cancelled by the corresponding signals stored during the first period.

3. A method for measuring blood flow in a limb of a living being comprising:
    (a) detecting blood flow signals at a first location along a limb of a living being;
    (b) applying uniform predetermined pressure around the circumference of the limb as close as possible to the first location, said pressure being applied for a first predetermined period of time and being sufficient to occlude the venous system in the limb while permitting systolic flow in the arterial system during said first period;
    (c) releasing the pressure on said limb for a second predetermined period of time that is long enough to allow a release of part of the blood that was pooled in the venous system on the distal side of said pressure application during said first period; and
    (d) cumulatively storing the detected blood flow signals for at least said second period to obtain a total blood flow value.

4. A method for measuring blood flow in a limb of a living being comprising:
    (a) detecting blood flow signals at a first location along a limb of a living being;
    (b) applying uniform predetermined pressure around the circumference of the limb near the first location, said pressure being applied for a first predetermined period of time equal to more than one heart cycle and being sufficient to occlude the venous system in the limb while permitting systolic flow in the arterial system during said first period;
    (c) releasing the pressure on said limb for a second predetermined period of time, the second period being shorter than the first period so as to allow a release of only a predetermined initial portion, with rapidly changing flow rate, of the blood that was pooled in the venous system on the distal side of said pressure application during said first period; and
    (d) cumulatively storing the detected blood flow signals for at least said second period to obtain a total blood flow value.

5. A method for measuring blood flow in a limb of a living being comprising:
    (a) detecting blood flow signals at a first location along a limb of a living being;
    (b) applying uniform predetermined pressure around the circumference of the limb as close as possible to the first location, said pressure being applied for a first predetermined period of time equal to more than one heart cycle and being sufficient to occlude the venous system in the limb while permitting systolic flow in the arterial system during said first period;
    (c) storing the detected blood flow signals for said first period;
    (d) releasing the pressure on said limb for a second predetermined period of time, the second period being shorter than the first period so as to allow a release of only a predetermined initial portion, having rapidly changing flow rate, of the blood that was pooled in the venous system on the distal side of said pressure application during said first period; and
    (e) subtracting the blood flow signals stored for a predetermined number of heart cycles during at least a part of the first period from the blood flow signals detected for an equal number of heart cycles during at least the second period; so that the arterial flow and local electrocardiac components of the decreasing blood flow signal during the second period are cancelled by the corresponding signals stored during the first period.

6. A method for measuring blood flow in a limb of a living being comprising:
    (a) detecting blood flow signals at a first location along a limb of a living being;
    (b) applying uniform predetermined pressure around the circumference of the limb as close as possible to the first location, said pressure being applied for a first predetermined period of time equal to more than one heart cycle and being less than the local diastolic pressure but sufficient to occlude the venous system in the limb while permitting systolic flow in the arterial system during said first period;
    (c) storing the detected blood flow signals for said first period;
    (d) releasing the pressure on said limb for a second predetermined period of time, the second period being shorter than the first period so as to allow a release of only a predetermined initial portion, with rapidly changing flow rate, of the blood that was pooled in the venous system on the distal side of said pressure application during said first period; and (e) subtracting the blood flow signals stored for a predetermined number of heart cycles during at least a part of the first period from the blood flow signals detected for an equal number of heart cycles during at least the second period; so that the arterial flow and local electrocardiac components of the decreasing blood flow signal during the second period are cancelled by the corresponding signals stored during the first period.

7. A method for measuring blood flow in a limb of a living being comprising:
   (a) detecting blood flow signals at a first location along a limb of a living being;
   (b) applying uniform predetermined pressure around the circumference of the limb as close as possible to the first location, said pressure being applied for a first predetemined period of time equal to a plurality of heart cycles and being less than the local diastolic pressure but sufficient to occlude the venous system in the limb while permitting systolic flow in the arterial system during said first period;
   (c) storing the detected blood flow signals for said first period;
   (d) releasing the pressure on said limb for a second predetermined period of time, the second period being shorter than the first period so as to allow a release of only a predetermined initial portion, having rapidly changing flow rate, of the blood that was pooled in the venous system on the distal side of said pressure application during said first period; and
   (e) subtracting the blood flow signals stored for a predetermined number of heart cycles during a part of the first period from the blood flow signals detected for an equal number of heart cycles during at least the second period by inverting the signals detected for at least the second period and combining the inverted signals with the signals stored during the part of the first period; so that the arterial flow and local electrocardiac components of the exponentially decreasing blood flow signal during the second period are cancelled by the corresponding signals stored during the first period.

8. A method for measuring blood flow in a limb of a living being comprising:
   (a) detecting blood flow signals at a first location along a limb of a living being;
   (b) detecting electrocardiac signals of the living being for use as synchronizing and clocking signals;
   (c) generating a triggering signal at the end of each successive count of a predetermined number of electrocardiac signals detected in step (b), each triggering signal being synchronized with a R-wave of a corresponding electrocardiac cycle;
   (d) applying uniform predetermined pressure around the circumference of the limb as close as possible to the first location, said pressure being applied in response to each triggering signal for a first predetermined period of time and being sufficient to occlude the venous system in the limb while permitting systolic flow in the arterial system during said first period;
   (e) delaying each triggering signal by a time equal to the first predetermined time period of step (d);
   (f) releasing the pressure on said limb in response to each delayed triggering signal for a second predetermined period of time that is shorter than the first period of time to allow a release of part of the blood that was pooled in the venous system on the distal side of said pressure application during said first period; and
   (g) cumulatively storing the detected blood flow signals for at least said second period to obtain a total blood flow value.

9. A method for measuring blood flow in a limb of a living being comprising:
   (a) detecting blood flow signals at a first location along a limb of a living being;
   (b) detecting electrocardiac signals of the living being for use as synchronizing and clocking signals;
   (c) generating a triggering signal at the end of each successive count of a predetermined number of electrocardiac signals detected in step (b), each triggering signal being synchronized with an R-wave of a corresponding electrocardiac cycle;
   (d) applying uniform predetermined pressure around the circumference of the limb as close as possible to first location, said pressure being applied in response to each triggering signal for a first predetermined period of time and being sufficient to occlude the venous system in the limb while permitting systolic flow in the arterial system during said first period;
   (e) delaying each triggering signal by a time equal to the first predetermined time period of step (d);
   (f) releasing the pressure on said limb in response to each delayed triggering signal for a second predetermined period of time that is shorter than the first period of time to allow a release of part of the blood that was pooled in the venous system on the distal side of said pressure application during said first period, the time for each count of a predetermined number of heart cycles in step (c) being equal to at least the sum of said first and second periods of time; and
   (g) cumulatively storing the detected blood flow signals for at least said second period to obtain a total blood flow value.

10. Apparatus for measuring blood flow in a limb of a living being, the apparatus comprising:
    means adapted to apply uniform predetermined pressure around the circumference of a limb of a living being at a predetermined location, said uniform pressure being less than the local diastolic pressure at said location;
    first sensing means adapted to be placed adjacent to said location for detecting signals in response to blood flow in said blood vessels;
    second sensing means adapted to be placed on the skin of the living being at a location where a strong electrocardiac signal can be obtained for use as a synchronizing and timing signal;
    a trigger circuit connected to the second sensing means for providing a trigger pulse in synchronism with the R-wave of each heart cycle detected by the second sensing means;
    a counter having an input connected to the output of the trigger circuit, a first output for providing a first synchronizing pulse after counting a first predetermined number of trigger pulses from a selected initial pulse, and a second output for providing a second synchronizing pulse after counting a second predetermined number of trigger pulses from said selected initial pulse, the second predetermined number being greater than the first predetermined number;

an inverter connected to the first sensing means and the first output of the counter for alternately passing through unchanged and for reversing the polarity of said detected blood flow signals in response to successive first synchronizing pulses;

means coupled to the second output of the counter and responsive to each second synchronizing pulse for actuating the means for applying uniform pressure around the circumference of a limb;

a delay generator coupled to the second output of the counter for delaying each second synchronizing pulse for a predetermined time shorter than the interval between successive second synchronizing pulses;

means connected to the output of the delay generator and responsive to each delayed second synchronizing pulse for releasing the means for applying uniform pressure around the circumference of a limb; and means connected to the outputs of the inverter and the trigger circuit and coupled to the second output of the counter for processing the signals detected by the first sensing means for a predetermined number of heart cycles as determined by the counter.

11. Apparatus for measuring blood flow in a limb of a living being, the apparatus comprising:

means adapted to apply uniform predetermined pressure around the circumference of a limb of a living being at a predetermined location, said uniform pressure being less than the local diastolic pressure at said location;

first sensing means adapted to be placed adjacent to said location for detecting signals in response to blood flow in said blood vessels;

second sensing means adapted to be placed on the skin of the living being at a location where a strong electrocardiac signal can be obtained for use as a synchronizing and timing signal;

a trigger circuit connected to the second sensing means for providing a trigger pulse in synchronism with the R-wave of each heart cycle detected by the second sensing means;

a counter having an input connected to the output of the trigger circuit, a first output for providing a first synchronizing pulse after counting a first predetermined number of trigger pulses from a selected initial pulse, and a second output for providing a second synchronizing pulse after counting a second predetermined number of trigger pulses from said selected initial pulse, the second predetermined number being greater than the first predetermined number;

an inverter connected to the first sensing means and the first output of the counter for alternately passing through unchanged and for reversing the polarity of said detected blood flow signals in response to successive first synchronizing pulses;

a first delay generator connected to the second output of the counter for delaying the second synchronizing pulse for a predetermined time period;

means connected to the output of the first delay generator for actuating the means for applying uniform pressure around the circumference of the limb in response to each delayed synchronizing pulse;

a second delay generator connected to the output of the first delay generator for further delaying each second synchronizing pulse for a predetermined additional time shorter than the interval between successive second synchronizing pulses;

means connected to the output of the second delay generator and responsive to each further delayed second synchronizing pulse for releasing the means for applying uniform pressure around the circumference of a limb; and means connected to the outputs of the inverter, the trigger, and the first delay generator for processing the signals detected by the first sensing means for a predetermined number of heart cycles as determined by the counter.

12. Apparatus for measuring blood flow in a limb of a living being, the apparatus comprising:

a pressure cuff adapted to be wrapped around a limb of a living being at a predetermined location along the limb;

a source of air pressure connected to the cuff, the pressure being less than the local diastolic pressure at said location but sufficient to stop the flow of blood through the venous system at said location;

a first valve connected between the source of pressure and the cuff for selectively inflating the cuff;

an exhaust line connected to the cuff;

a second valve connected in the exhaust line for selectively releasing pressure from the cuff;

first sensing means adapted to be placed adjacent to said location for detecting signals in response to blood flow in said blood vessels;

second sensing means adapted to be placed on the skin of the living being at a location where a strong electrocardiac signal can be obtained for use as a synchronizing and timing signal;

a trigger circuit connected to the second sensing means for providing a trigger pulse in synchronism with the R-wave of each heart cycle detected by the second sensing means;

a counter having an input connected to the output of the trigger circuit, a first output for providing a first synchronizing pulse after counting a first predetermined number of trigger pulses from a selected initial pulse, and a second output for providing a second synchronizing pulse after counting a second predetermined number of trigger pulses from said selected initial pulse, the second predetermined number being greater than the first predetermined number;

an inverter connected to the first sensing means and the first output of the counter for alternately passing through unchanged and for reversing the polarity of said detected blood flow signals in response to successive first synchronizing pulses;

means coupled to the second output of the counter and responsive to each second synchronizing pulse for opening the first valve for applying said pressure to the cuff;

a delay generator coupled to the second output of the counter for delaying each second synchronizing pulse for a predetermined time shorter than the interval between successive second synchronizing pulses;

means connected to the output of the delay generator and responsive to each delayed second synchronizing pulse for opening the second valve for releasing the pressure from said cuff; and means connected to the outputs of the inverter and the trigger circuit and coupled to the second output of the counter for processing the signals detected by the first sensing means for a predetermined number of heart cycles as determined by the counter.

13. Apparatus for measuring blood flow in a limb of a living being, the apparatus comprising:

a pressure cuff adapted to be wrapped around a limb of a living being at a predetermined location along the limb;

a source of air pressure connected to the cuff, the pressure being less than the local diastolic pressure at said location but sufficient to stop the flow of blood through the venous system at said location;

a first valve connected between the source of pressure and the cuff for selectively inflating the cuff;

an exhaust line connected to the cuff;

a second valve connected in the exhaust line for selectively releasing pressure from the cuff;

first sensing means adapted to be placed adjacent to said location for detecting signals in response to blood flow in said blood vessels;

second sensing means adapted to be placed on the skin of the living being at a location where a strong electrocardiac signal can be obtained for use as a synchronizing and timing signal;

a trigger circuit connected to the second sensing means for providing a trigger pulse in synchronism with the R-wave of each heart cycle detected by the second sensing means;

a counter having an input connected to the output of the trigger circuit, a first output for providing a first synchronizing pulse after counting a first predetermined number of trigger pulses from a selected initial pulse, and a second output for providing a second synchronizing pulse after counting a second predetermined number of trigger pulses from said selected initial pulse, the second predetermined number being greater than the first predetermined number;

an inverter connected to the first sensing means and the first output of the counter for alternately passing through unchanged and for reversing the polarity of said detected blood flow signals in response to successive first synchronizing pulses;

a first delay generator connected to the second output of the counter for delaying the second synchronizing pulse for a predetermined time period;

means connected to the output of the first delay generator for opening the first valve for applying said pressure to the cuff in response to each delayed synchronizing pulse;

a second delay generator connected to the output of the first delay generator for further delaying each second synchronizing pulse for a predetermined additional time shorter than the interval between successive second synchronizing pulses;

means connected to the output of the second delay generator and responsive to each further delayed synchronizing pulse for open the second valve for releasing the pressure from the cuff; and means connected to the outputs of the inverter, the trigger, and the first delay generator for processing the signals detected by the first sensing means for a predetermined number of heart cycles as determined by the counter.

* * * * *